United States Patent [19]

Schumacher et al.

[11] Patent Number: 5,153,138

[45] Date of Patent: Oct. 6, 1992

[54] PYRUVATE OXIDASE MUTANTS, DNA EXPRESSING PYRUVATE OXIDASE AND METHODS OF USE THEREOF

[75] Inventors: Günther Schumacher, Bernried; Hans Moellering, Tutzing, both of Fed. Rep. of Germany

[73] Assignee: Boehringer Mannheim GmbH, Mannheim, Fed. Rep. of Germany

[21] Appl. No.: 736,683

[22] Filed: Jul. 26, 1991

Related U.S. Application Data

[60] Division of Ser. No. 670,362, Mar. 14, 1991, Pat. No. 5,096,821, which is a continuation of Ser. No. 416,593, Oct. 3, 1989, abandoned.

[30] Foreign Application Priority Data

Oct. 3, 1988 [DE] Fed. Rep. of Germany ....... 3833601

[51] Int. Cl.⁵ ............ C12N 15/00; C12N 9/02; C12N 9/06; C07H 15/12
[52] U.S. Cl. ................ 435/320.1; 435/189; 435/191; 435/172.1; 536/27
[58] Field of Search .............. 435/320.1, 189, 191, 435/172.1; 536/27

[56] References Cited

U.S. PATENT DOCUMENTS 4,666,832 5/1987 Elstner et al. .............. 435/25

OTHER PUBLICATIONS

Suggs et al., PNAS, vol. 78, No. 11, Nov. 1981, pp. 6613-6617.

*Primary Examiner*—Robert A. Wax
*Assistant Examiner*—Keith D. Hendricks
*Attorney, Agent, or Firm*—Felfe & Lynch

[57] ABSTRACT

The present invention provides a pyruvate oxidase which decarboxylates pyruvate to form inter alia hydrogen peroxide and is active without the addition of FAD, thiamine pyrophosphate and divalent metal ions. The amino acid sequence of the enzyme changes at least one proline in position 178 and alanine in position 458 to a different amino acid. The present invention also provides a process for the preparation of this pyruvate oxidase and methods of use thereof.

9 Claims, 4 Drawing Sheets

FIG. 1A

```
  1  ATGGTTATGAAACAAACAAAACAAACTAACATACTAGCCAGGTGCAGCAGTTATTAAAGTT    60
     MetValMetLysGlnThrLysGlnThrAsnIleLeuAlaGlyAlaAlaValIleLysVal

61  TTAGAAGCTTGGGGAGTAGATCATTGTATGGTATTCCTGAGGTTCAATTAATTCAATT    120
     LeuGluAlaTrpGlyValAspHisLeuTyrGlyLysIleProGlySerIleAsnSerIle

121  ATGGACGCATTATCAGCAGAAAGGGATCGAATCCATTATATTCAAGTACGGCATGAAGAA    180
     MetAspAlaLeuSerAlaGluArgAspArgIleHisTyrIleGlnValArgHisGluGlu

181  GTTGGTGCAATGGCCGCCGCTGATGCTAAGCTAACGGGTAAAATCGGGGTTTGCTTC    240
     ValGlyAlaMetAlaAlaAlaAspAlaLysLeuThrGlyLysIleGlyValCysPhe

241  GGCTCAGCGGGACCTGGTGGCACTCATCTTATGAATGGGTTATATGATGCGCGTGAAGAC    300
     GlySerAlaGlyProGlyGlyThrHisLeuMetAsnGlyLeuTyrAspAlaArgGluAsp

301  CATGTCCCTGTTCTAGCACTTATTGGTCAATTGGAACTACTGGATGAACATGGATACG    360
     HisValProValLeuAlaLeuIleGlyGlnPheGlyThrThrGlyMetAsnMetAspThr

361  TTCCAAGAAATGAATGAGAATCCGATTTATGCGGACGTTGCAGATTATAATGTAACAGCC    420
     PheGlnGluMetAsnGluAsnProIleTyrAlaAspValAlaAspTyrAsnValThrAla

421  GTCAATGCTGCCACGTTGCCACATGTTATTGACGAAGCAATTCGACGCGCCTACGCGCAC    480
     ValAsnAlaAlaThrLeuProHisValIleAspGluAlaIleArgArgAlaTyrAlaHis

481  CAAGGTGTTGCGGTTGTGCAAATTCCAGTCGATTTACCATGGCAACAGATTCCAGCTGAA    540
     GlnGlyValAlaValValGlnIleProValAspLeuProTrpGlnIleProAlaGlu
```

FIG. 1B

```
541   GATTGGTATGCTTCCGCTAATAGTTATCAAACGCCGTTATTACCAGAACCCGACGTTCAA   600
      AspTrpTyrAlaSerAlaAsnSerTyrGlnThrProLeuLeuProGluProAspValGln

601   GCAGTGACGAGATTGACACAGACTTACTCGCAGTGAACGGCCACTTATTACTATATGGC   660
      AlaValThrArgLeuThrGlnThrLeuLeuAlaAlaGluArgProLeuIleTyrTyrGly

661   ATTGGAGCTCGTAAGGCTGTAAAGAACTCGAACAATTGAGTAAAACGTTGAAAATTCCA   720
      IleGlyAlaArgLysAlaGlyLysGluLeuGluGlnLeuSerLysThrLeuLysIlePro

721   TTAATGAGTACGTATCCAGCTAAGGGTATTGTCGCGGATCGTTATCCAGCCTATTTGGGT   780
      LeuMetSerThrTyrProAlaLysGlyIleValAlaAspArgTyrProAlaTyrLeuGly

781   TCTGCTAATCGGGTGGCACAAAAACCGGCGAATGAGGCACTTGCGCAAGCCGACGTTGTT   840
      SerAlaAsnArgValAlaGlnLysProAlaAsnGluAlaLeuAlaGlnAlaAspValVal

841   TTATTGTTGGTAATAATTATCCGTTGCAGAAGTTCCAAAGCGTTTAAAAATACGCGT   900
      LeuPheValGlyAsnAsnTyrProPheAlaGluValSerLysAlaPheLysAsnThrArg

901   TATTCTTACAAATTGATATTGATCCGCTAAGTAGGTAAACGACATAAAACAGATATT   960
      TyrPheLeuGlnIleAspIleAspProAlaLysLeuGlyLysArgHisLysThrAspIle

961   GCGGTACTTGCTGATGCACAAAAGACGCTGGCTGCAATTTAGCACAGGTATCTGAACGG   1020
      AlaValLeuAlaAspAlaGlnLysThrLeuAlaAlaIleLeuAlaGlnValSerGluArg

1021  GAGTCGACACCTTGGTGGCAAGCCAATTAGCCAATGTTAAAAAATTGGCGGCTTATCTA   1080
      GluSerThrProTrpTrpGlnAlaAsnLeuAlaAsnValLysAsnTrpArgAlaTyrLeu
```

FIG. 1C

```
1081  GCTTCATTAGAAGATAAGCAGGAAGGGCCTTTACAAGCATATCAAGTGCTACGTGCGGTT    1140
      AlaSerLeuGluAspLysGlnGluGlyProLeuGlnAlaTyrGlnValLeuArgAlaVal

1141  AATAAAATTGCGGAGCCTGATGCAATCTATTCGATTGTTGGTGATATCAATTGAAT      1200
      AsnLysIleAlaGluProAspAlaIleTyrSerIleAspValGlyAspIleAsnLeuAsn

1201  GCGAATCGACATTTGAAATTAACGCCATCCAATGGCACATTACTTCTAACTTATTGCT    1260
      AlaAsnArgHisLeuLysLeuThrProSerAsnArgHisIleThrSerAsnLeuPheAla

1261  ACGATGGAGTTGGTATTCCCGGAGCAATTGCTGCCAAACTTAATTATCCTGAGCGGCAG    1320
      ThrMetGlyValGlyIleProGlyAlaIleAlaAlaLysLeuAsnTyrProGluArgGln

1321  GTGTTAATCTGGCCGGTGATGGTGGCGCTTCGATGACCATGCAAGATTTGGCGACGCAA    1380
      ValLeuAsnLeuAlaGlyAspGlyGlyAlaSerMetThrMetGlnAspLeuAlaThrGln

1381  GTTCAATACCATTACCAGTGATTAAATGTTGTTTCCAACTGCCAATATGGATTATC      1440
      ValGlnTyrHisLeuProValIleAsnValValPheThrAsnCysGlnTyrGlyPheIle

1441  AAAGATGAGGAAGATACTAATACAAGATGATTTTATGGCTCAAGCTTTTCAGTTAATGATATT   1500
      LysAspGluGluAspThrAsnGlnAsnAspPheIleGluValGluPheAsnLysIleGlu

1501  GATTTTAGTAAGATTGCCGATGGCCAAGCTTTCAGTTAATAAGAACCAGTTCTGATT      1560
      AspPheSerLysIleAlaAspGlyValHisMetGlnAlaPheArgValAsnLysIleGlu

1561  CAATTACCTGATGTTTGAACAAGCAATCGCTCAGCAGATCAGCTTAGATTCGGCA         1620
      GlnLeuProAspValPheGluGlnAlaLysAlaIleAlaGlnHisGluProValLeuIle

1621  GATGCGGTGATTACAGGAGATCGGCCACTGCCTGAAAAGCTTCGTTAGATTCGGCA       1680
      AspAlaValIleThrGlyAspArgProLeuProAlaGluLysLeuArgLeuAspSerAla

1681  ATGAGTTCGGACTGATATTGAAGCATTAAACAACGGTATGAAGCTCAAGATTACAA      1740
      MetSerSerAlaAlaAspIleGluAlaPheLysGlnArgTyrGluAlaGlnAspLeuGln

1741  CCACTTCAACTTATTAAAACAATTTGGCTTAGATGATTGCAACATCAAATTGACAG     1800
      ProLeuSerThrTyrLeuLysGlnPheGlyLeuAspAspLeuGlnHisGlnIleGlyGln

1801  GGTGGGTTTAA    1812
      GlyGlyPheEnd
```

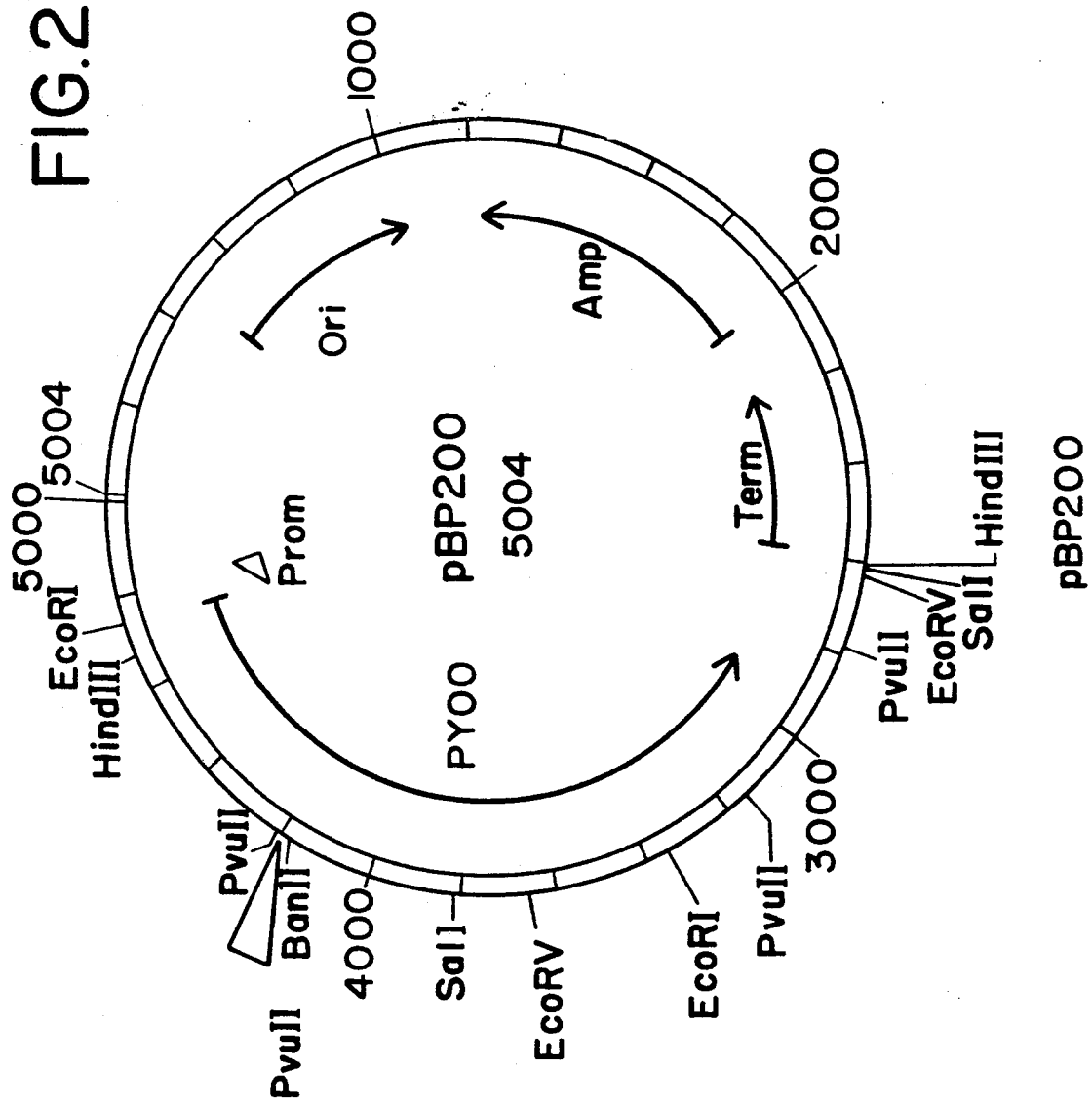

PYRUVATE OXIDASE MUTANTS, DNA EXPRESSING PYRUVATE OXIDASE AND METHODS OF USE THEREOF

This is a Divisional Application of application Ser. No. 07/670,362, filed Mar. 14, 1991, now U.S. Pat. No. 5,096,821; which is a continuation of application Ser. No. 07/416,593, filed Oct. 3, 1989, now abandoned.

The present invention is concerned with pyruvate oxidase mutants, processes for the preparation thereof and reagents containing said mutants for the determination of pyruvate.

More particularly, the present invention is concerned with mutants of pyruvate oxidase which are more stable than the wild type enzyme and, therefore, are better suited for the enzymatic determination of pyruvate and of reactions which give rise to pyruvate.

Pyruvate oxidase (E.C. 1;2;3;3) is an enzyme which decarboxylates pyruvate in the presence of phosphate ions ("Pi") and oxygen with the formation of hydrogen peroxide (*Federation Proceedings*, 13, 734-738/1954). The reaction products, i.e., acetyl phosphate, carbon dioxide and especially hydrogen peroxide, can readily be detected analytically and, therefore, this enzyme is suitable for the quantitative determination of pyruvate and pyruvate-forming enzymes and of their substrates.

U.S. Pat. No. 4,666,832 teaches a pyruvate oxidase which is active without the addition of FAD, thiamine pyrophosphate (TPP) and divalent metal ions. In the presence of serum and magnesium ions, this enzyme does not form any insoluble precipitates and possesses excellent storage stability. However, it has been shown that in the presence of high salt concentrations in the serum, as well as at pH values of >7, this pyruvate oxidase only has limited stability.

Surprisingly, we have now found mutants of pyruvate oxidase from *Lactobacillus plantarum* (DSM 2571) which have better stability toward salts and in the alkaline pH range as compared to known forms of pyruvate oxidase.

Thus, according to the present invention, a mutant pyruvate oxidase is provided which decarboxylates pyruvate to form hydrogen peroxide and is active without the addition of FAD, thiamine pyrophosphate and divalent metal ions, characterized by at least one change selected from the group consisting of a change from proline in position 178 and alanine in position 458.

Especially preferred is a mutant enzyme having serine at position 178 and/or valine at position 458 of the amino acid sequence.

The mutant enzyme is characterized by a molecular weight of 250,000 (determined in an ultracentrifuge according to Ames), a pH optimum of 6.5 and $K_m$ with pyruvate (25° C.) of about 0.4 mmole/liter and a $K_m$ with phosphate (25° C.) of about 2.3 mmole/liter.

The mutant enzyme possesses residual activity of at least 45% in 0.1 mole/liter potassium phosphate buffer (pH 8) with 0.15 mole/liter sodium chloride after 30 minutes at 25° C.

Under these conditions, the preferred mutant enzyme shows residual activity of at least 70%. An especially preferred mutant enzyme displays residual activity of at least 85% under these conditions.

The preparation of the mutant enzymes according to the present invention takes place in that, according to known recombinant gene technology, a recombinant DNA which contains a pyruvate oxidase gene with essentially the sequence of the wild type enzyme (see FIG. 1 of the accompanying drawings) but additionally at least one change in the nucleotide base sequence at one of positions 532, 533, 534, 1372, 1373, and 1374 is incorporated into an expression vector. This change results in expression of a different amino acid in the position listed (i.e., 178 or 458). An appropriate host strain is transformed with this vector and is selected on the basis of expression of the expression vector. The thus transformed and selected strain is cultured under appropriate conditions and the mutant enzyme recovered from the culture medium.

The recombinant DNA preferably contains DNA where C (cystein) has been substituted by T (thymine) at at least one of bases 532 and base 1373, as compared to the nucleotide base sequence expressing known pyruvate oxidase.

The present invention also provides recombinant DNA which contains a pyruvate oxidase gene having a change in the nucleotide base sequence at one of positions 532, 533, 534, 1372, 1373 and 1374 as compared to the nucleotide base sequence expressing known pyruvate oxidase. Base 532 and/or base 1373 is preferably exchanged. Substitution of C for T at these positions is preferred.

However, any other substitution which results in the substitution of the amino acid at position 178 (proline) or the amino acid at position 458 (alanine) by any other amino acid is also covered herein. Substitution by serine (178) and valine (425) is especially preferred.

As recombinant DNA, especially preferred are plasmids pBP 201, pBP 202, pBP 203, pBP 203a and pBP 2006.

As host systems, both gram-positive and gram-negative micro-organisms can be used. Examples are *Bacillus spec.* or *Escherichia coli*. Micro-organisms of the species *Escherichia coli* are especially preferred. In particular, micro-organisms *Escherichia coli* laq Iq, (DSM 3689), (ED 8654), (DSM 2102), *Escherichia coli*, (DSM 4105), and *Escherichia coli*, (DMS 4106) are preferred. Vectors such as pBR 322 and derivatives are especially preferred as expression plasmids.

The present invention also provides the plasmids pBP 201, pBP 202, pBP 203, pBP 203 and pBP 2006. These contains the pyruvate oxidase gene of the wild, i.e., the known type (see FIG. 1) having changes in their DNA sequence as follows:

|  | base 532 from C to T | base 1274 from C to T | Change in 500 bp Ban II-EcoRV fragment |
|---|---|---|---|
| pBP 201 | + | − | − |
| pBP 202 | + | − | + |
| pBP 203 | + | + | − |
| pBP 203a | − | + | − |
| pBP 2006 | + | + | + |

The present invention also provides the DNA sequence of the wild type pyruvate oxidase which was not known until now. This DNA is contained in plasmid pBP 200 and is suitable as starting material for the preparation of the recombinant DNA according to the present invention.

The present invention is also concerned with the use of the mutant enzymes according to the present invention for the determination of pyruvate, pyruvate-forming enzymes and substrates thereof.

The determination of pyruvate preferably takes place by measuring hydrogen peroxide formed in the reaction scheme elaborated herein. Numerous suitable methods are known for this purpose which do not have to be described here in detail. It is also possible to measure the consumption of oxygen, for example by means of an oxygen electrode.

Typical examples of determinations which can be carried out with the enzyme according to the present invention are described in European Patent Specification No. 0,274,425 and include, for example, determination of glutamate-pyruvate transaminase, α-ketoglutarate, glutamate-oxalacetate transminase, pyruvate kinase, ADP, lactate dehydrogenase, lactic acid, glycerol, glycerol phosphate kinase, triglycerides, creatine phosphokinase, creatine, myokinase, thiokinase and fatty acids.

The present invention also provides a reagent for the determination of pyruvate which contains mutant enzymes according to the present invention, phosphate, a system for the determination of hydrogen peroxide, a buffer, and optionally a system for the formation of pyruvate.

As buffer there can be used any suitable buffer substance which buffers in the pH range of from about 5 to 9. Phosphate buffer is especially suitable. When a phosphate buffer is used, a separate source of inorganic phosophate is not required. In choosing the buffer, the pH values necessary for the adjuvant enzymes present in the system and other ingredients, such as chromophores must be considered. However, on the basis of the data known for these enzymes, an appropriate choice of buffer can readily be made by the skilled artisan.

The reagent according to the present invention is also suitable for the impregnation of carrier materials, for example papers, synthetic resins, films and the like, for making test strips.

The reagent according to the present invention preferably contains 1-50 U/ml mutant enzyme and 10-500 mmole/liter phosphate (pH 6-8).

The following examples are given for the purpose of illustrating the present invention.

EXAMPLE 1

Cells of *Escherichia coli* ED lac I$^q$, DSM 3689 which contain one of the plasmids pBP 201, pBP 202, pBP 203, pBP 203a or pBP 2006 are cultured overnight at 28° to 30° C. in a 1 liter fermenter. As medium, there is used a complete medium (yeast/peptone extract) which contains 0.4% lactose and 100 mmole/liter phosphate (pH 7.5).

After centrifuging for 15 minutes at 8000 r.p.m., the cells are digested with lysozyme and the pyruvate oxidase is purified over DEAE-Sephadex and gel filtration (Sephacryl S 200).

EXAMPLE 2

Testing of the stability of the Enzyme in salt solution a) Activity determination

To test the stability of the enzyme, first the activity of the enzyme is determined on the basis of the following reactions:

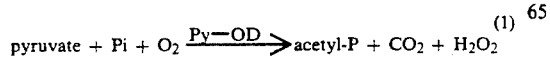

$$\text{pyruvate} + P_i + O_2 \xrightarrow{\text{Py-OD}} \text{acetyl-P} + CO_2 + H_2O_2 \quad (1)$$

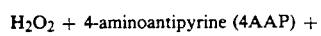

$H_2O_2$ + 4-aminoantipyrine (4AAP) + (2)

-continued

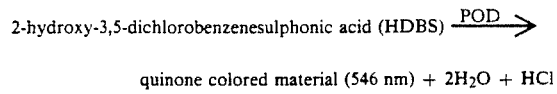

2-hydroxy-3,5-dichlorobenzenesulphonic acid (HDBS) $\xrightarrow{\text{POD}}$ quinone colored material (546 nm) + $2H_2O$ + HCl Hydrogen peroxide is consumed in equimolar amount relative to the colored material 1 U Py-OD=1 μmole pyruvate reaction/min at 25° C.

The determination of the activity of the pyruvate oxidase (Py-OD) takes place with a reagent consisting of (end concentration in the test): 72 mmole/liter potassium phosphate buffer (pH 6.7); 8 mmole/liter 4-AAP; 6.8 mmole/liter HDBS; 50 mmole/liter pyruvate and 10 U/ml peroxidase (POD).

To 2 ml of this reagent is added 0.1 ml of the pyruvate oxidase solution to be tested and at 546 nm the extinction change per minute (ΔE/min) is determined at 25° C. with an optical path length of the solution of 1 cm. (ε=16.5 cm²/umole). The activity is calculated according to the following equation:

$$\text{activity } (U) = \frac{\Delta E/\text{min} \times V}{\epsilon}$$

V = cuvette volume (cm³).

b) Stressing at pH 7.5

Pyruvate oxidase is stressed in an incubation solution consisting of 0.1 mole/liter potassium phosphate buffer (pH 7.5) and 0.15 mole/liter sodium chloride at 25° C. or 37° C. over the time given in the following Table I and the activity is determined in the manner described in Example 2(a). The results obtained are to be seen in Tables I/II. FIG. 2 of the accompanying drawings shows the results obtained after stressing at 37° C. for 20 hours at different pH values in 0.1 mole/liter potassium phosphate buffer. It follows therefrom that the pyruvate oxidases coded by the plasmids according to the present invention are superior to the wild type enzyme. The mutant pBP 2006, in particular, shows high stability towards alkaline pH values and to salts.

TABLE I

| enzyme | temperature 25° C. % residual activity after | |
|---|---|---|
| | 10 min | 30 min |
| wide type | 28 | 5 |
| mutants | | |
| pBP 201 | 65 | 45 |
| pBP 202 | 89 | 70 |
| pBP 203 | 84 | 76 |
| pBP 2006 | 98 | 86 |

TABLE II

| enzyme | temperature 37° C. % residual activity after | | |
|---|---|---|---|
| | 5 min | 10 min | 20 min |
| wild type | 4 | 0 | 0 |
| mutants | | | |
| pBP 202 | 48 | 19 | 4 |
| pBP 203 | 45 | 18 | 5 |
| pBP 2006 | 65 | 36 | 34 |

EXAMPLE 3

Testing of the enzyme stability with undiluted serum 9.5 ml of undiluted serum are adjusted to the pH values given in the following Table III by the dropwise addition of 10% acetic acid or 2 mole/liter aqueous sodium hydroxide solution. Subsequently, 0.5 ml pyruvate oxidase solution (150 U/ml) is added thereto and a stressing at 37° C. carried out. The determination of the residual activity takes place as described in Example 2(a). The following Table III shows the results obtained.

TABLE III

| | residual activity after | | | | | |
|---|---|---|---|---|---|---|
| | 1 min | 2 min | 5 min | 1 min | 2 min | 5 min |
| pH value | wide type enzyme | | | pBP 2006 | | |
| 5.92 | 103 | 93.5 | 71.2 | 93.4 | 86.4 | 73.2 |
| 6.45 | 96.0 | 95.1 | 90.2 | 98.1 | 88.6 | 90.6 |
| 6.98 | 90.9 | 71.5 | 17.5 | 92.4 | 82.9 | 77.9 |
| 7.58 | 67.5 | 26.9 | 1.5 | 81.2 | 78.7 | 53.1 |
| 8.08 | 36.2 | 6.5 | — | 87.0 | 78.2 | 21.8 |
| 8.71 | 1.3 | — | — | 90.3 | 78.6 | 31.6 |

EXAMPLE 4

Testing of the stability of pyruvate oxidase from plasmid pBP 203a

Colonies of Escherichia coli laq I<sup>q</sup>, DSM 3689, with and without plasmid pBP 203a, are cultured overnight on complete medium with cellulose filters. Subsequently, lysis is carried out with chloroform/toluene and the filters incubated for 20 minutes at 37° C. in 0.1 mole/liter potassium phosphate buffer (pH 7.5) and 0.15 mole/liter sodium chloride. The filters are then applied to plates which contain an indicator medium consisting of 40 mmole/liter sodium pyruvate, 0.24 mg/liter 4-aminoantipyrine, 1.5 mg/ml. N-ethyl-N-(3-methylphenyl)2-aminoethanesulphonic acid (EST), 1.25 µg/ml peroxidase, 1% agar and 50 mmole/liter potassium phosphate buffer (pH 7.2) and the color reaction observed after 1 minute. It is found that only colonies of micro-organisms which contain pBP 203a give a color reaction and consequently pyruvate oxidase is still present. The micro-organisms which contain the wild type plasmid no longer show a color reaction. This means that the pyruvate oxidase mutants from pBP 203a also show superior stability in comparison with the wild type enzyme.

EXAMPLE 5

Preparation of pyruvate oxidase mutant enzymes

Starting from the plasmid pBP 200 (DSM 4875) (production according to Example 6) which contains the wild type gene of pyruvate oxidase, the corresponding mutation is carried out on the DNA template with the method of directed mutagenesis. This process is described in detail in Proc. Nat. Acad. Sci. USA, 82, 488-492/1985 and Nat. Enzymol. 1987, as well as in Bulletin 1313 of Biorad Laboratories, Richmond, U.S.A. to Muta-Gene ® in vitro mutagenesis kit.

For the preparation of pBP 201, oligonucleotide A with the following sequence was used:

5'-CGTTCAGCTGAAATCTGTTG-3'

For the preparation of pBP 203a, oligonucleotide B with the following sequence was used:

5'-AACTTGCGTCACCAAATCTT-3'

For the preparation of pBP 203, oligonucleotides A and B were used.

Plasmid pBP 202 which, like pBP 201, has a change of C to T at base, 532, has, in addition a mutation on a 500 bp BanII/EcoRV fragment of the wild type gene. This plasmid has been deposited at the German Collection for Micro-organisms (DSM).

The plasmid pBP 2006 was prepared from pBP 202 by directed mutagenesis with the use of oligonucleotide B.

Further mutant enzymes are prepared by the use of oligonucleotide C:

5'-CGTTCAGCGCTAATCTGTTG-3', (changing proline at 178 for serine) of oligonucleotide D:

5'-CGTTCAGCGACAATCTGTTG-3'

(changing proline at 178 for valine) of oligonucleotide E:

5'-CGTTCAGCAGCAATCTGTTG-3'

(changing proline at 178 for alanine) of oligonucleotide F:

5'-AACTTGCGTGGTCAAATCTT-3'

(changing alanine at 458 for threonine) of oligonucleotide G:

5'-AACTTGCGTAAGCAAATCTT-3'

(changing at alanine 458 for leucine of oligonucleotide H:

5'-AACTTGCGTGCCAAATCTT-3'

(changing of alanine 458 for glycine.

EXAMPLE 6

Preparation of pBP 200 (DSM 4875)

Plasmid pKK177-3 (DSM 3026) is cleaved with EcoRI and SmaI to form a first fragment. From the pyruvate oxidase-coding DNA fragment (FIG. 1) an approximately 1 kb EcoRI-SalI fragment and an approximately 1.2 kb SalI-Eco RV fragment are isolated. All three fragments are ligated with one another. This ligated product is transformed in Escherichia coli (DSM 3689) and selected for ampicillin resistance. The plasmid pBP 200 coding the pyruvate oxidase carries the restriction sites as given in FIG. 3 of the accompanying drawings.

Plasmid pBP 200 can also be obtained from plasmid pBP 202 by deletion of an approximately 2.2 kb-sized EcoRI-Eco RV fragment and replacement of this fragment by an approximately 1 kb-sized EcoRI-SalI and an approximately 1.2 kb-sized SalI-EcoRV fragment of the DNA according to FIG. 1 of the accompanying drawings.

It will be understood that the specification and examples are illustrative but not limitative of the present invention and that other embodiments within the spirit and scope of the invention will suggest themselves to those skilled in the art.

We claim:

1. An Isolated DNA molecule having a sequence which codes for a mutant pyruvate oxidase which pyruvate oxidase, is characterized by activity in the absence of FAD, thiamine pyrophosphate and divalent metal ions, and which differs in its amino acid sequence as compared to wild type pyruvate oxidase in at least one of amino acid position 178 and position 458 of FIG. 1.

2. The Isolated DNA molecule of claim 1, wherein said sequence coding for a mutant pyruvate oxidase which differs at amino acid positions 178 and 458 as compared to wild type pyruvate oxidase.

3. The Isolated DNA molecule of claim 1, wherein said sequence codes for serine at amino acid position 178 of said pyruvate oxidase.

4. The Isolated DNA molecule of claim 1, wherein said sequence codes for valine at amino acid position 458 of said pyruvate oxidase.

5. Plasmid pBP 201.

6. Plasmid pBP 202 (DSM 4861).

7. Plasmid pBP 203.

8. Plasmid pBP 203a.

9. Plasmid pBP 2006.

* * * * *

UNITED STATES PATENT AND TRADEMARK OFFICE
CERTIFICATE OF CORRECTION

PATENT NO.    : 5,153,138
DATED         : October 6, 1992
INVENTOR(S)   : Gunther Schumacher et al.

It is certified that error appears in the above-identified patent and that said Letters Patent is hereby corrected as shown below:

Column 2, line 31: change "valine (425)" to -- valine (458) --.

Signed and Sealed this

Eighth Day of March, 1994

Attest:

BRUCE LEHMAN

Attesting Officer

Commissioner of Patents and Trademarks